United States Patent
Raju et al.

(10) Patent No.: US 7,780,997 B2
(45) Date of Patent: Aug. 24, 2010

(54) PHARMACEUTICALLY ACTIVE EXTRACTS OF VITEX LEUCOXYLON, A PROCESS OF EXTRACTING THE SAME AND A METHOD OF TREATING DIABETES AND INFLAMMATORY DISEASES THEREWITH

(75) Inventors: Gokaraju Ganga Raju, Andhra Pradesh (IN); Gokaraju Rama Raju, Andhra Pradesh (IN); Gottumukkala Venkata Subbaraju, Andhra Pradesh (IN); Somepalli Venkateswarlu, Andhra Pradesh (IN)

(73) Assignee: Laila Impex, Andhra Pradesh (IN)

( * ) Notice: Subject to any disclaimer, the term of this patent is extended or adjusted under 35 U.S.C. 154(b) by 0 days.

(21) Appl. No.: 12/065,599

(22) PCT Filed: Sep. 5, 2005

(86) PCT No.: PCT/IN2005/000299

§ 371 (c)(1),
(2), (4) Date: Mar. 3, 2008

(87) PCT Pub. No.: WO2007/029263

PCT Pub. Date: Mar. 15, 2007

(65) Prior Publication Data

US 2008/0199543 A1    Aug. 21, 2008

(51) Int. Cl.
*A61K 36/00* (2006.01)
(52) U.S. Cl. ...................................... 424/725
(58) Field of Classification Search ....................... None
See application file for complete search history.

(56) References Cited

U.S. PATENT DOCUMENTS

| 6,242,012 B1 | 6/2001 | Newmark et al. |
| 2003/0054058 A1 | 3/2003 | Corley et al. |

OTHER PUBLICATIONS

Miura et al. Corosolic Acid Induces Glut4 Translocation in Genetically Type 2 Diabetic Mice. Biol Pharm. Bull. 27(7) 1103-1105. 2004.*

* cited by examiner

*Primary Examiner*—Christopher R Tate
*Assistant Examiner*—Melenie McCormick
(74) *Attorney, Agent, or Firm*—Fitch, Even, Tabin & Flannery

(57) ABSTRACT

The present invention relates to pharmaceutically active extracts of *Vitex leucoxylon* exhibiting hypoglycemic and anti-inflammatory properties. This extract is suitable for administrating to animals and humans in treating diabetes, liver disorders and related inflammatory diseases. The extract is found suitable for treating insulin and non-insulin diabetes mellitus.

6 Claims, No Drawings

PHARMACEUTICALLY ACTIVE EXTRACTS OF VITEX LEUCOXYLON, A PROCESS OF EXTRACTING THE SAME AND A METHOD OF TREATING DIABETES AND INFLAMMATORY DISEASES THEREWITH

TECHNICAL FIELD OF THE INVENTION

The present invention provides a new, non-toxic *Vitex leucoxylon* extract for inhibiting increase of blood sugar level or lowering blood glucose levels and a process for extracting the same from the plant material. Isolated corosolic acid from the extract is also useful for inhibiting increase of blood sugar level. This plant extract reduces accumulation of triglyceride in the treatment of diabetes and related conditions. This extract also exhibits anti-inflammatory activity and is found to contain corosolic acid, agnuside and a new compound, 6-O-caffeoylarbutin.

Diabetes mellitus is a common, serious disease characterized by hyperglycemia. This disease can be divided into two major subclasses: insulin-dependent diabetes mellitus (IDDM), also known as type I diabetes, and non-insulin-dependent diabetes mellitus (NIDDM), also known as type II diabetes. According to the American Diabetes Association, diabetes mellitus is estimated to effect approximately 6% of the world population. Untreated, diabetes can lead to very serious chronic problems, including heart disease, kidney failure, blindness, nerve damage and other problems (Porte, D. et al., *Science,* 1996, 27, 699-700).

There are a number of agents currently available in the market for diabetes management, which belongs to various structural types. For example, thiazolidinediones, sulfonyl ureas, alpha-glucosidase inhibitors, biguanides are some of the drug types currently available in the market. In the natural products arena, a handful of herbal medications were proven to be effective against this terrible menace. For example, Fenugreek (*Trigonella foenumgraecum*), Gymnema (*Gymnema sylvestre*), Jamun/Jambolan (*Syzygium cumini*), Bitter melon/Karela (*Momordica charantia*) and Banaba (*Lagerstroemia speciosa*) are some of the products known to exhibit hypoglycemic activity. Natural antidiabetic treatments have gained popularity in the recent years because of their proven safety from long history of usage in traditional medicine and also present usage in herbal treatments.

Corosolic acid (FIG. 1, 2α-hydroxyursolic acid, CAS No. 4547-24-4), a triterpenoid compound present in Banaba (*Lagerstroemia speciosa* L.) and in other plants was found to possess antidiabetic activity (Judy, W. V. et. al., *J. Ethnopharmacol.,* 2003, 87, 115-117 & Matsuyama, U.S. Pat. No. 6,485,760, 2002).

FIG. 1: corosolic acid

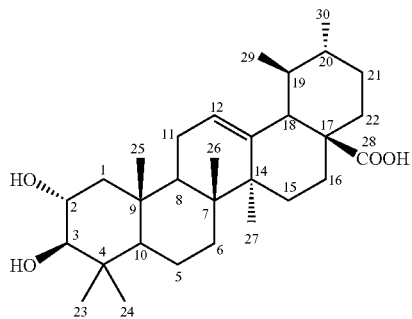

Inflammation is a critical biological process caused by injury, infection, swelling and also due to age related factors and this process is known to occur by increased metabolic activity of archidonic acid, which leads into two main pathways, the cyclooxygenase (COX) and lipoxygenase (LOX). Steroidal and non-steroidal anti-inflammatory drugs are most commonly used remedies for these diseases, but most of the drugs available in the market are known to cause side effects.

Free radicals play a major role in the progression of a wide range of pathological disturbances and lead to very serious problems like cancer, Alzheimer's, Parkinson's, and cardiovascular diseases. In the food industry, free radicals have been found to be responsible for the deterioration of food during processing and storage. In view of this, considerable attention has been given to the addition of antioxidants in foods and supplementation of antioxidants to biological systems to scavenge free radicals.

BACKGROUND OF THE INVENTION

Proven safety of herbal product and the absence of a single herbal extract capable of addressing the problems discussed herein above, lead to the present invention. Herbal extracts, specifically the extract obtained from *Vitex leucoxylon* is found to treat diabetic conditions, inflammatory diseases, liver disorders and free radical mediated diseases.

DISCLOSURE OF THE INVENTION

The present invention relates to pharmaceutically active extracts of *Vitex leucoxylon* extracting hypoglycemic and anti-inflammatory properties. This extract is suitable for administrating to animals and humans in treating diabetes, liver disorders and related inflammatory diseases. The extract is found suitable for treating insulin and non-insulin diabetes mellitus.

Another aspect of this invention is directed to a process for extracting pharmaceutically active principles from *Vitex leucoxylon.* This extract is found to contain corosolic acid represented by FIG. 1.

FIG. 1: corosolic acid

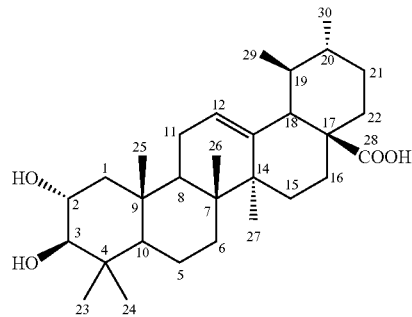

This extract exhibits hypoglycemic activity.

Corosolic acid may be separated from this extract by column chromatography and subsequent crystallization.

Yet another object of this invention involves a method of treating hyperglycemia and non-insulin dependent diabetes mellitus (NIDDM) in animals by administering the extract obtained from *Vitex leucoxylon.*

The extract of this plant exhibits anti-inflammatory and hepatoprotective activities in addition to its hypoglycemic action.

This invention is also directed to isolation of agnuside and a new arbutin derivative 6-O-caffeolarbutin in its pure form from the plant extract by subjecting it to column chromatography and subsequent purification.

The other object of the present invention is a process for manufacturing an extract from *Vitex leucoxylon* plant, wherein the extract has anti-inflammatory and hepatoprotective activities in addition to hypoglycemic activity and contains corosolic acid, agnuside (FIG. 2) and 6-O-caffeoylarbutin (FIG. 3).

Other object of the present invention is a method for isolating agnuside and a new arbutin derivative, 6-O-caffeoylarbutin in pure form by column chromatography, followed by crystallization.

SUMMARY OF THE INVENTION

This invention relates to pharmaceutically effective extracts exhibiting hypoglycemic and anti-inflammatory activity in mammals obtained from all species of *Vitex*, particularly, *Vitex leucoxylon*.

All parts of the plant species may be used for extraction but leaves are preferred.

This invention also includes a method of obtaining pharmaceutically effective extracts from species of *Vitex* which comprises the steps of drying and powdering the plant material, extracting the same with polar or non-polar solvents removing insolubles therefrom and distilling the solvent to obtain pharmaceutically effective extracts.

Extracts maybe obtained from *Vitex leucoxylon, Vitex agnus-castus, Vitex rotundifolia, Vitex trifolia* and *Vitex altissima*. The extract may also be admixed with other known pharmaceutically effective compounds exhibiting hypoglycemic action. Pure corosolic acid having up to 100% purity may be obtained from the crude extract by subjecting it to chromatographic separation and crystallization.

This invention further includes a method for treating diabetic and inflammatory conditions by administering an extract obtained from plant species *Vitex*, particularly from *Vitex leucoxylon*.

DETAILED DISCLOSURE OF THE INVENTION

*Vitex leucoxylon* Linn., belongs to genus *Vitex* (Family: Verbenaceae) is a small to large tree with a short thick trunk and found throughout the Deccan peninsula. The plant grows, for instance, in the hilly area of Chittor district of Andhra Pradesh, India, where it typically flowers and bears fruits (cream colored) during March to April. Descriptions of *Vitex leucoxylon* plant can be found in "The wealth of India—A dictionary of Indian raw materials and industrial products", CSIR: New Delhi, 1976, 10, 522. The hepatoprotective and anti-inflammatory activities of *Vitex negundo* have been patented (US pat. Application No. 20040029816, Feb. 12, 2004) and these activities are attributed to the iridoid glycoside namely, agnuside. The roots and the bark of *Vitex leucoxylon* Linn are astringent and roots are used as a febrifuge. The leaves are smoked for relieving headache and catarrh and are also used for medicinal baths in fevers and anemia (Nadkami, A. K., *Indian Materia Medica*, Popular Book Depot., Mumbai, 1976, 1, 1278-1280). The ethanolic extract of *Vitex leucoxylon* leaves shows comparable anti-inflammatory activity to that of *Vitex negundo* at the dose of 400 mg/kg and the extract is 3 times less toxic than that of *Vitex negundo* extract (Makwana, H. G. et al., *Indian J. Physiol. Pharmacol.*, 1994, 38, 95-100). The plant has not been studied thoroughly and there is only one report on the chemical constituents of this plant, it contains flavonoids and aromatic compounds (Krishna Rao, R. V. et. al., *Indian Drugs*, 1997, 34, 50-51.

Other species of *Vitex* include *Vitex negundo, Vitex agnus-castus, Vitex rotundifolia, Vitex trifolia, Vitex altissima*, etc. However, there are no reports earlier that *Vitex leucoxylon* or other *Vitex* species contains corosolic acid in sufficient quantity to treat hyperglycemic conditions.

The present invention relates to a process for manufacturing a *Vitex leucoxylon* extract that possesses hypoglycemic activity and contains corosolic acid in varying concentrations. All species of the *Vitex* can be used for producing an active extract; more particularly *Vitex leucoxylon* and all parts of the plant can be used, but preferably, leaves.

The invention also relates to a process for isolating corosolic acid in highly purified form by column chromatography using polar and non-polar solvents as eluents, followed by crystallizations. The isolated pure corosolic acid structure (FIG. 1) has been confirmed by HPLC of the standard obtained from banaba leaves and also by its physical and spectral data (IR, NMR and mass).

The present invention also envisions a manufacturing process of an active extract from the plant *Vitex leucoxylon* and the said extract has hypoglycemic activity.

The method comprises (a) Drying the leaves in powder form, (b) Percolating the powder about 3-5 times with polar or non-polar solvents, (c) Boiling the powder with the percolated solvent and filtering to remove insoluble particles, (d) Evaporating the solvent under vacuum to get an active extract, and it contains corosolic acid ranging between 0.5 and 2%, (e) The extract is partitioned with other solvents to enrich the extract to contain corosolic acid in the range of 2-10%.

(f) Isolating the pure compound corosolic acid by column chromatography, and (g) Obtaining the corosolic acid in the range of 90-100% purity by crystallizations using polar or non-polar solvents.

The invention described the *Vitex leucoxylon* extract containing corosolic acid compound in the range of 0.1-100%, using the above process steps, more particularly 1% corosolic acid.

The invention also described the method of treating diabetic conditions by the use of *Vitex leucoxylon* extract containing 1% corosolic acid and the activity was supported by the measurement of hypoglycemic activity. From the percentage of inhibitory values (Shown in table I) of the present inventive *Vitex leucoxylon* extract showed potent hypoglycemic activity and the activity is superior to that of existing commercial banaba extracts containing 1% corosolic acid.

Moreover, the *Vitex leucoxylon* extract contains negligible amount of congeneric maslinic acid, an inactive triterpenoid, whereas the banaba extract contains significant amounts of masclinic acid. Thus, isolation of corosolic acid in highly pure form from the banaba extract is very difficult and requires repeated column chromatography and crystallizations. Whereas, in our present invention *Vitex leucoxylon* extract, isolation of corosolic acid in highly pure form is commercially feasible.

The invention also relates to a process for isolating agnuside (FIG. 2) in highly purified form by column chromatography, followed by crystallizations. The isolated pure agnuside structure has been confirmed by its physical and spectral data (IR, NMR and mass).

FIG. 2: Agnuside

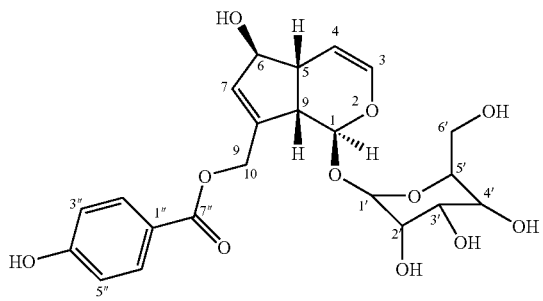

The *Vitex leucoxylon* extract of this invention contains this new compound, 6-O-caffeoylarbutin in addition to agnuside and corosolic acid in the range of 0.1-10%. The extract by the above process contains about 1% of 6-O-caffeoylarbutin.

The invention also describes the use of *Vitex leucoxylon* extract containing 1% corosolic acid and 2% agnuside for treating anti-inflammatory conditions. The anti-inflammatory activity was demonstrated by the carrageenan paw edema method. From the data of Table 2, it is clear that the present inventive *Vitex leucoxylon* extract showed significant anti-inflammatory activity.

The invention also describes the use of corosolic acid in pure form (90-100%) from the said *Vitex leucoxylon* extract, for treating diabetic and inflammatory conditions.

Because of proven hepatoprotective activity of agnuside, the present inventive *Vitex leucoxylon* extract containing corosolic acid (1%) and agnuside (2%) could be used for treating the liver disorders.

This invention also relates to a process for isolating a new compound, 6-O-caffeoylarbutin (Formula 3) in highly purified form by column chromatography, followed by crystallizations. The isolated pure 6-caffeoylarbutin structure has been confirmed by its physical and spectral data (IR, NMR and mass).

Formula 3

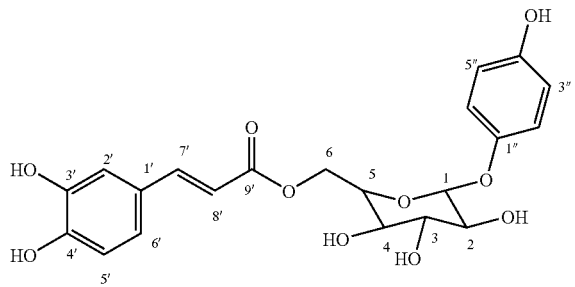

*Vitex leucoxylon* extract of this invention contains this new compound, 6-O-caffeoylarbutin in addition to agnuside and corosolic acid in the range of 0.1-10%. The extract by the above process contains about 1% of 6-O-caffeoylarbutin.

This invention also describes the use of *Vitex leucoxylon* extract containing corosolic acid (1%), agnuside (2%) and 6-O-caffeoylarbutin (1%) in preventing free radical mediated diseases. The antioxidative activity was measured by two standard in vitro assays (a) Superoxide free radical NBT (Nitroblue tetrazolium) and (b) DPPH free radical scavenging methods. From the $IC_{50}$ values (Table 3), the present inventive *Vitex leucoxylon* extract showed strong antioxidative activity and it is superior to the commercially available antioxidants, BHT (Butylated hydroxytoluene) and Vitamin C.

A further aspect of the present invention is a pharmaceutical formulation comprising an extract as described above in a pharmaceutically acceptable carrier (e.g., an aqueous or a non aqueous carrier).

A still further aspect of the present invention is a method of treating diabetes, comprising administering to a human or animal subject in need thereof a treatment effective amount (e.g., an amount effective to treat slow the progression of, etc.) of an extract as described above.

The invention is described in the examples given below which are provided by a way of illustrations only and should not be construed to limit the scope of the present invention.

EXAMPLES

Example 1

Preparation of the *Vitex leucoxylon* extract, containing 1% corosolic acid: 11.5 Kg (0.1 to 0.5% of corosolic acid) of *Vitex leucoxylon* (leaf) is shade dried and powdered. The powdered plant material was boiled with aqueous ethanol (90%, 5×15 L) for 10 h. The combined alcohol extract was filtered through supercell to remove insoluble plant material. The solvent was distilled, dried to give powdered material (2.43 Kg).

Analytical results of the extract: 1 gram of the powder concentrate obtained in the above (1) was dissolved in methanol (10 mL) and analyzed by high-performance liquid chromatography (HPLC) to show, corosolic acid content 10 mg (1%, RT: 6.709 min) in the above concentrate (corresponding to 1 mg of corosolic acid per 100 mg of the concentrate) and agnuside content 20 mg (2%, RT: 6.667 min), 6-O-caffeoylarbutin content 10 mg (1%, RT: 10.037 min) in the above concentrate (corresponding to 2 mg of agnuside and 1 mg of 6-O-caffeoylarbutin per 100 mg of the concentrate).

Activity: The dose of streptozotocin is used to induce diabetes mimicking to NIDDM, encountered clinically in majority of patients. The NIDDM diabetic rats when treated with alcoholic extract of the plant *Vitex leucoxylon*, orally for 2-3 weeks recovered to normal state, whereas the rats of control NIDDM diabetic group continued to have diabetes and died in due course of time. The hypoglycaemic activity was also recorded with this extract powder (see table 1).

Example 2

Preparation of the extract, containing 2% corosolic acid: 7.5 Kg (0.22% of corosolic acid) of *Vitex leucoxylon* (leaf) is shade dried and powdered. The powdered plant material was boiled with hexane (5×10 L) for 10 h and filtered to remove oil impurities. The remaining material was boiled with ethyl acetate (5×10 L) for 10 h and the combined ethyl acetate extract was filtered through supercell. The solvent was distilled and the residue was vacuum dried to give powder material (430 g, HPLC: 2% corosolic acid) and the recovery is 54%.

Example 3

Preparation of the extract, containing 3% corosolic acid: The *Vitex leucoxylon* extract from example 1 (100 g, 1% corosolic acid) was stirred in water (800 mL) at rt for 10 h and filtered the soluble impurities. The insoluble powder was dried to give 10.8 g, as brown powder. HPLC: corosolic acid is 3.2% and the recovery is 35%.

Example 4

Preparation of the extract, containing 10% corosolic acid: A mixture of *Vitex leucoxylon* extract from example 1, containing 1% corosolic acid (100 g) and aqueous methanol (500 mL, 90%) was stirred at rt for 15 min and filtered the solid to get corosolic acid enriched *Vitex leucoxylon* extract as off-white powder (8 g). HPLC: corosolic acid is 10% and the recovery is 80%.

Example 5

Preparation of the extract, containing 12.7% corosolic acid: A mixture of *Vitex leucoxylon* extract from example 1, containing 1% corosolic acid (50 g), methanol (5 mL) and aqueous potassium hydroxide (50 mL, 1%) was stirred at rt for 15 min and stirred at 80° C. for 30 min. The cooled solution was filtered and the solid was washed with water (until the filtrate is neutral) to get corosolic acid enriched *Vitex Leucoxylon* extract as light green powder (3 g). HPLC: corosolic acid is 12.73% and the recovery is 76%.

Example 6

Isolation of pure corosolic acid: The *Vitex leucoxylon* extract (1 Kg, 1% corosolic acid) from example 1, was adsorbed over silica gel (100-200 mesh, 2 Kg) and chromatographed over silica gel column using chloroform-methanol (95:5) as eluents to give pure corosolic acid, which was crystallized from ethanol as colorless powder (10 g, 50% recovery), m.p. 242-244° C., $[\alpha]_D$: +41.1 (c, 0.9 in pyridine); $^1$H NMR (400 MHz, pyridine-$d_5$): δ 0.98 (3H, d, J=6.6 Hz, H-29), 0.99 (3H, s, H-25), 1.00 (3H, d, J=6.2 Hz, H-30), 1.01 (3H, s, H-24), 1.09 (3H, s, H-26), 1.22 (3H, s, H-27), 1.29 (3H, s, H-23), 2.64 (1H, d, J=6.8 Hz, H-18), 3.42 (1H, d, J=9.7 Hz, H-3α), 4.11 (1H, t, J=3.9, 9.7 Hz, H-2β), 5.47 (1H, t, J=3.5 Hz, H-12); MS (ESI, negative ion mode): m/z 471 (M-H)$^-$.

Example 7

Isolation of agnuside: The *Vitex leucoxylon* extract (0.5 Kg, 2% agnuside) from example 1, was adsorbed over silica gel (100-200 mesh, 1 Kg) and chromatographed over silica gel column using chloroform-methanol (90:10) as eluents to give agnuside, which was crystallized from chloroform-methanol as light yellow plates (7 g, 50% recovery), m.p. 148-150° C.; IR (KBr): 3406, 1702, 1658, 1608, 1276, 1168, 1104, 1077 cm$^{-1}$; $^1$H NMR (200 MHz, CD$_3$OD): δ 2.55 (1H, m, H-5), 2.90 (1H, m, H-9), 3.00-3.70 (4H, m, H-2',3',4',5'), 3.72 (2H, d, J=4.8 Hz, H-6'), 4.35 (1H, m, H-6), 4.60 (1H, d, J=7.5 Hz, H-1'), 4.80 (1H, m, H-1) 4.90-4.94 (2H, m, H-10), 5.05 (1H, dd, J=6.6, 4.2 Hz, H-4), 5.79 (1H, br s, H-7), 6.25 (1H, dd, J=6.6, 1.8 Hz, H-3), 6.75 (2H, d, J=8.4 Hz, H-3", H-5"), 7.80 (2H, J=8.4 Hz, H-2", H-6"); $^{13}$C NMR: δ 46.3 (C-5), 47.8 (C-9), 62.8 (C-6'), 63.7 (C-10), 71.5 (C-4'), 71.9 (C-2'), 77.9 (C-3'), 78.2 (C-5'), 82.9 (C-6), 98.0 (C-1), 100.2 (C-1'), 105.6 (C-4), 116.3 (C-3",5"), 122.0 (C-1"), 132.5 (C-7), 132.9 (C-2",6"), 141.7 (C-3), 142.9 (C-8), 162.7 (C-4"), 165.9 (C-7"); MS (ESI, negative ion mode): m/z 465 (M-H)$^-$.

Example 8

Isolation of 6-O-caffeoylarbutin [3,4,5-trihydroxy-6-(4-hydroxyphenoxy)-perhydro-2H-pyran-2-yl]methyl(2E)-3-(3,4-dihydroxyphenyl-2-enoate]: The *Vitex leucoxylon* extract (0.5 Kg, 1% 6-O-caffeoylarbutin) from example 1, was adsorbed over silica gel (100-200 mesh, 1 Kg) and chromatographed over silica gel column using chloroform-methanol (95:5) as eluents to give 6-O-caffeoylarbutin, which was crystallized from chloroform-methanol as light yellow plates (2.5 g, 50% recovery), m.p. 224-225° C.; IR (KBr): 3377, 1692, 1605, 1359, 1280, 1075, 826 cm$^{-1}$; $^1$H NMR (600 MHz, CD$_3$OD): δ 3.41-3.51 (3H, m, H-2,3,4), 3.65 (1H, m, H-5), 4.35 (1H, dd, J=12.0, 7.2 Hz, H-6b), 4.52 (1H, dd, J=12.0, 2.4 Hz, H-6a), 4.74 (1H, d, J=7.2 Hz, H-1), 6.27 (1H, d, J=15.6 Hz, H-8'), 6.65 (2H, d, J=9.0 Hz, H-3",5"), 6.78 (1H, d, J=8.4 Hz, H-5'), 6.92 (1H, dd, J=8.4, 1.8 Hz, H-6'), 6.94 (2H, d, J=9.0 Hz, H-2",6"), 7.05 (1H, d, J=1.8 Hz, H-2'), 7.56 (1H, d, J=15.6 Hz, H-7'); $^{13}$C NMR: δ 63.5 (C-6), 70.6 (C-4), 73.7 (C-2), 74.2 (C-5), 76.6 (C-3), 102.4 (C-1), 113.7 (C-8'), 113.9 (C-2'), 115.4 (C-5'), 115.5 (C-3", 5"), 118.4 (C-2", 6"), 122.1 (C-6'), 126.5 (C-1'), 145.6 (C-3'), 146.1 (C-7'), 148.4 (C-4'), 151.1 (C-1"), 152.6 (C-4"), 167.9 (C-9'); MS (ESI, negative ion mode): m/z 433 (M-H)$^-$.

Toxicity:

To assess the potential safety of *Vitex leucoxylon* (1% corosolic acid, 2% agnuside and 1% 6-O-caffeoylarbutin) extract, acute oral toxicity was conducted using updown procedure on rats.

The *Vitex leucoxylon* (1% corosolic acid, 2% agnuside and 1% 6-O-caffeoylarbutin) extract was administered to three healthy female rats orally at a dose of 5,000 mg/kg of body weight. The animals were observed for mortality, signs of gross toxicity, and behavioral changes at least once daily for 14 days. All animals survived, gained weight and appeared active and healthy. Also, gross necropsy on the subject rats at terminal sacrifice was unremarkable. The results showed that *Vitex leucoxylon* extract had no acute oral toxicity at 5,000 mg/kg, the maximum dosage mandated for testing under applicable FDA regulations.

Hypoglycemic activity: Hypoglycemic activity was tested by the inhibition of sucrose-induced raise in serum glucose levels (SGL), by the *V. leucoxylon* extracts in Albino wistar rats. The procedure involves fasting the rats for overnight at ad libitum water, numbered weighed and randomly divided into groups of three animals each. Prior to treatment blood samples were drawn from sinus orbital plexus of all animals using heparin coated glass capillaries under mild ether anesthesia. The blood samples were tested for serum glucose levels using enzymatic GOD/POD method. Optical densities were measured at 500 nm, SGL was calculated as follows. SGL=(test OD/Standard OD)×100 and the results were expressed in mg/dL. All the groups were treated orally with corresponding test substances, standard, vehicle (5% gum acacia). After 30 minutes, all animals were given 20 mL/kg of 20% sucrose solution orally using gastric tube. One hour after treatment, blood samples were drawn again under mild ether anesthesia and tested for serum glucose levels in a similar procedure as described above for initial serum glucose estimation. The data was subjected to statistical treatment using t-test and inhibitory rate was calculated by comparing mean increase in serum glucose levels of control and red groups.

Anti-inflammatory activity (Carrageenin induced paw edema method): Prior to the experiment all the animals (Albino wistar rats of either sex weighing between 180-300 g) fasted at ad libitum water and were weighed, numbered and randomly divided into groups, each containing 3 animals. Initial paw volumes were measured using plethesmometer and noted. All the groups were treated with corresponding test substance orally using gastric tube. Control group was treated with 10 mL/Kg vehicle (0.5%, carboxymethyl cellulose sodium salt). After 30 minutes, all the animals were injected subcutaneously at subplantar region of left hind paw 1% carrageenin 0.1 mL using hypodermic needle. All the animals were administered water 20 mL/Kg body weight and kept devoid of water for 3 h (maintained uniform hydration). After 3 h, paw volumes of all the animals were measured twice and average volume from two measurements were recorded. The % of inhibition of paw edema was calculated by comparing paw edema of test substance treated groups with that of control groups.

Antioxidant Activity (a) Superoxide free radical-scavenging activity. The superoxide free radical-scavenging activity was determined by the NBT (nitro blue tetrazolium) method. The reaction mixture contained EDTA (6.6 mM), NaCN (3 µg), riboflavin (2 µM), NBT (50 µM), various concentrations of the test drug in ethanol and a phosphate buffer (58 mM, pH 7.8) in a final volume of 3 mL. Optical density was measured at 560 nm. The test tubes were uniformly illuminated with an incandescent lamp for 15 min, after which the optical density was measured again at 560 nm. The percentage inhibition and superoxide radical generation was measured by comparing the absorbance values of the control and those of the test compounds.

(b) DPPH free radical scavenging activity. DPPH (1,1-diphenyl-2-picryl-hydrazyl) radical scavenging activity was measured based on the reduction of methanolic solution of the colored DPPH. Free radical scavenging ability of the test drug in ethanol added to the methanolic solution of DPPH is inversely proportional to the difference in initial and final absorption of DPPH solution at 516 nm. The reaction mixture contained $1 \times 10^{-4}$ nm methanolic solution of DPPH and various concentrations of test drugs. The percentage inhibition was determined by comparing the absorbance values of test and control tubes.

TABLE 1

Hypoglycemic activity

| S. No | Compound Name | Oral dose in mg/Kg | Increased SGL (mean ± SE) | % of inhibition | t-value |
|---|---|---|---|---|---|
| 1 | Control | 5% GA | 30.72 ± 2.36 | — | — |
| 2 | Corosolic acid | 1 mg | 27.72 ± 3.27 | 9.78 | 2.04 |
| 3 | Banaba extract (1% corosolic acid) | 50 mg | 20.12 ± 5.84 | 34.49 | 1.68 |
| 4 | Vitex leucoxylon extract (1% corosolic acid) | 50 mg | 17.28 ± 1.71 | 43.75 | 4.61 |
| 5 | Vitex leucoxylon extract (2% corosolic acid) | 50 mg | 17.01 ± 5.22 | 44.61 | 2.39 |
| 6 | Vitex leucoxylon extract (10% corosolic acid) | 10 mg | 17.86 ± 1.82 | 41.86 | 4.32 |
| 7 | Glibenclamide | 25 mg | 6.12 ± 4.32 | 80.0 | 3.45 |

TABLE 2

Anti-inflammatory activity (Carrageenan induced paw edema)

| S. No. | Compound Name | Oral dose in mg/Kg | % of inhibition |
|---|---|---|---|
| 1 | Control | — | — |
| 2 | Banaba extract (1% corosolic acid) | 250 mg | 26.20 |
| 3 | Vitex leucoxylon extract (1% corosolic acid) | 250 mg | 26.20 |
| 4 | Vitex leucoxylon extract (2% corosolic acid) | 250 mg | 22.25 |
| 5 | Vitex leucoxylon extract (10% corosolic acid) | 100 mg | 32.11 |
| 6 | Diclofenac sodium | 25 mg | 63.10 |

TABLE 3

Antioxidant activity

| S. No. | Compound Name | Superoxide (NBT) scavenging activity ($IC_{50}$ µg/mL) | DPPH radical scavenging activity ($IC_{50}$ µg/mL) |
|---|---|---|---|
| 1 | Vitex leucoxylon extract (1% corosolic acid) | 44.5 | 7.4 |
| 2 | Vitex leucoxylon extract (2% corosolic acid) | 34.0 | 9.6 |
| 3 | Vitex leucoxylon extract (10% corosolic acid) | — | 13.0 |
| 4 | BHA | 966 | 18 |
| 5 | Vitamin C | 852 | 14 |

It is evident that the extract after removal of solvents therefrom may be administered along with pharmaceutically acceptable adjutants.

The invention claimed is:

1. A method of reducing blood sugar levels or treating diabetes in a mammal in need thereof comprising administering a pharmaceutically effective dosage of an extract from a *Vitex* plant species to the mammal, wherein the extract includes corosolic acid and at least one compound selected from the group consisting of anguside and 6-O-caffeoylarbutin and wherein the *Vitex* species is selected from the group consisting of *Vitex leucoxylon* Linn, *Vitex agnus-castus* Linn, *Vitex rotundifolia* Linn, *Vitex trifolia* Linn, *Vitex altissima* Linn, and mixtures thereof.

2. The method of claim 1, wherein the extract is obtained by a process comprising:
   drying parts of *Vitex* plant species;
   powdering the dry plant parts to obtain a powder;
   repeatedly percolating the powder with polar and/or nonpolar solvents to obtain a percolate;
   heating the percolate;
   removing insolubles from the percolate; and
   separating solvent from the percolate.

3. The method of treating diseases as claimed in claim 1, wherein the extract of *Vitex* species is in admixture with compounds selected from the group consisting of pharmaceutically acceptable carriers, adjutants, binders and mixtures thereof.

4. The method of claim 1, wherein the extract includes at least 0.1% by weight of corosolic acid and at least 0.1% by weight of anguside.

5. The method of claim 1, wherein the extract includes at least 0.1% by weight of corosolic acid, at least 0.1% by weight of anguside and at least 0.1% by weight of 6-O-caffeoylarbutin.

6. The method of claim 1, wherein the extract is obtained by a process comprising:

i) drying parts of the *Vitex* plant species;

ii) powdering the dry plant parts to obtain a powder;

iii) repeatedly percolating the powder with non-polar and/or polar solvents to obtain a percolate;

iv) heating the percolate at ambient temperature;

v) removing insolubles from the percolate; and vi) separating solvent from the percolate.

* * * * *